United States Patent [19]
Soss

[11] Patent Number: 5,272,908
[45] Date of Patent: Dec. 28, 1993

[54] FLAME POSITION ULTRASONIC INTERFEROMETER

[75] Inventor: David A. Soss, Salt Lake City, Utah

[73] Assignee: The United States of America as represented by the Secretary of the Navy, Washington, D.C.

[21] Appl. No.: 474,695

[22] Filed: Feb. 6, 1990

Related U.S. Application Data

[63] Continuation of Ser. No. 82,780, Jul. 27, 1987, abandoned.

[51] Int. Cl.$^5$ .............................................. G01N 33/22
[52] U.S. Cl. ............................................................ 73/35
[58] Field of Search ............... 73/598, 602, 597, 629, 73/628, 625, 116, 35; 367/99, 101, 129, 124, 125; 60/254, 253, 234

[56] References Cited

U.S. PATENT DOCUMENTS

| | | | |
|---|---|---|---|
| Re. 30,088 | 9/1979 | Lund et al. | 73/622 |
| 3,815,358 | 6/1974 | Younkin | 60/234 |
| 3,839,801 | 10/1974 | Herz | 60/234 |
| 3,899,919 | 8/1975 | Geisler et al. | 73/35 R |
| 4,022,055 | 5/1977 | Flournoy et al. | 73/627 |
| 4,409,821 | 10/1983 | Battles et al. | 73/116 |
| 4,413,517 | 11/1983 | Soden | 73/597 |
| 4,522,064 | 6/1985 | McMillan | 73/592 |
| 4,545,249 | 10/1985 | Matay | 73/597 |
| 4,624,142 | 11/1986 | Heyman | 73/597 |

Primary Examiner—Robert Raevis
Attorney, Agent, or Firm—Kenneth L. Warsh

[57] ABSTRACT

A sensitive instrument system for determining the position of the burn front in a rocket motor is disclosed. Separate adjacent transmitter and receiver elements are attached to the rocket motor casing to form an ultrasonic interference system. An ultrasound beam is transmitted to the motor's interior and the reflected beam from the propellant gas burn front is captured by the receiver. The received signal is processed to determine the distance to the propellant-gas interface.

12 Claims, 3 Drawing Sheets

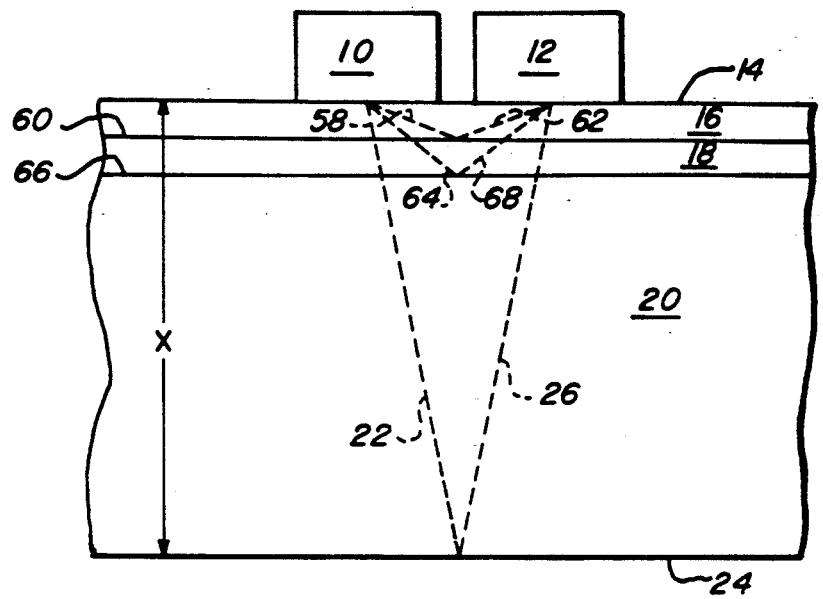
FIG._1
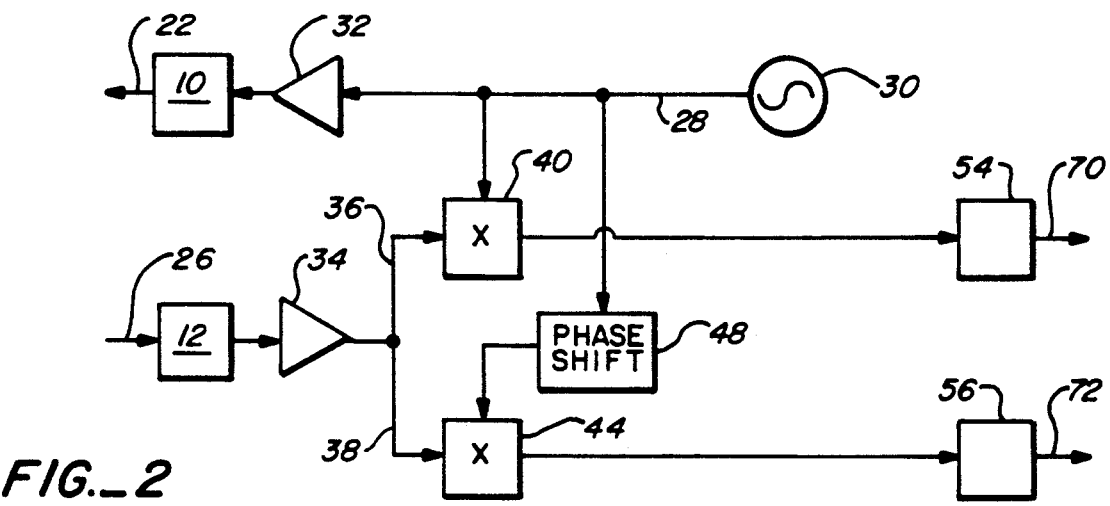
FIG._2
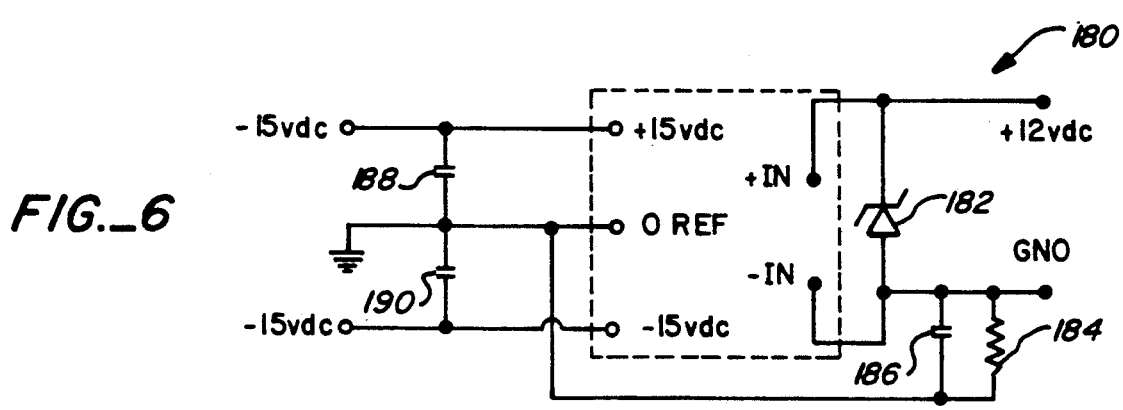
FIG._6

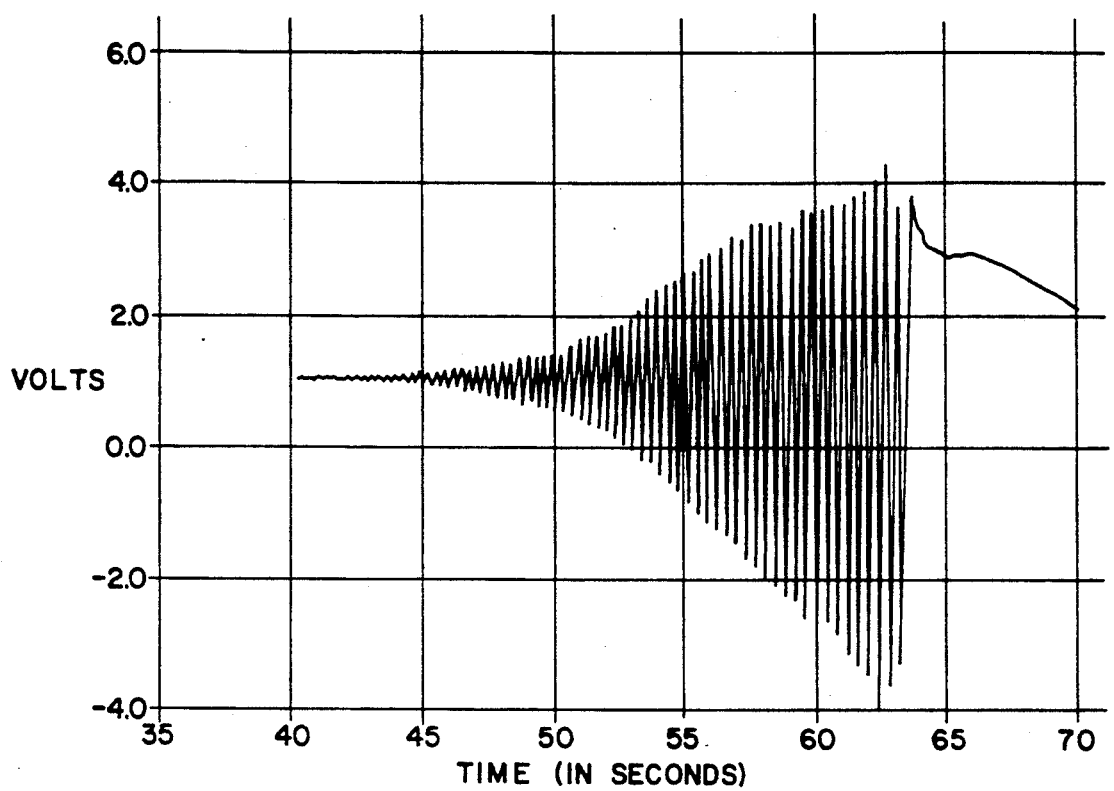
FIG._3
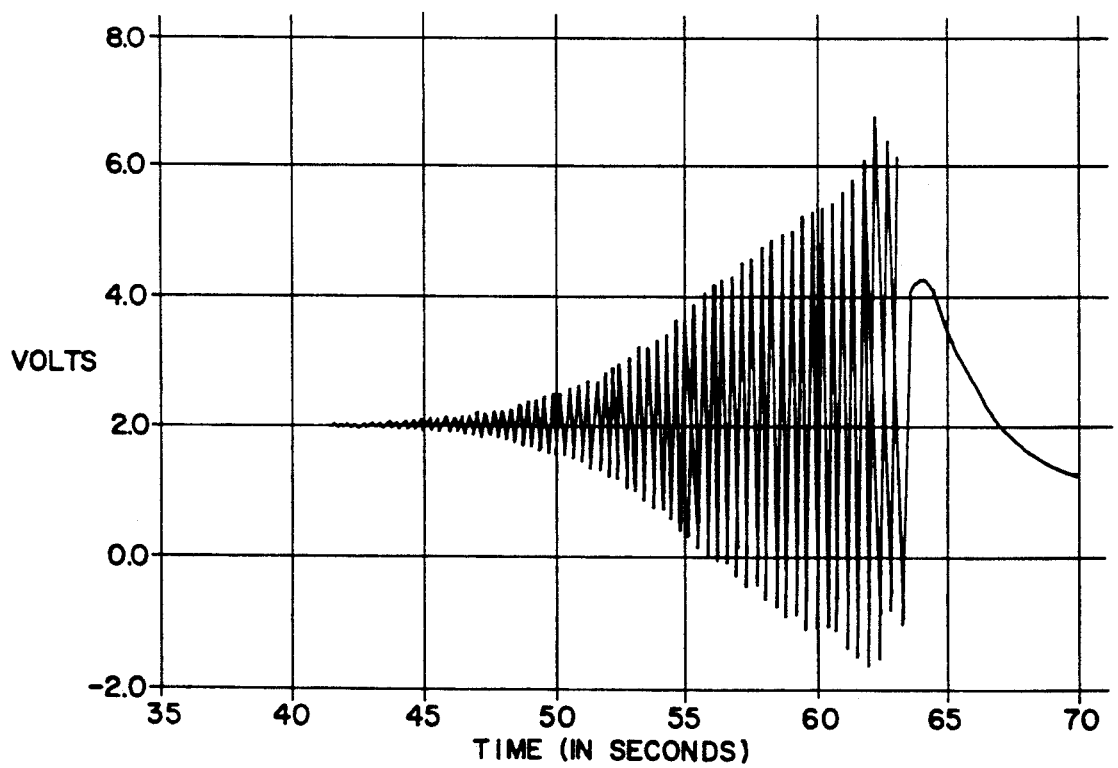
FIG._4

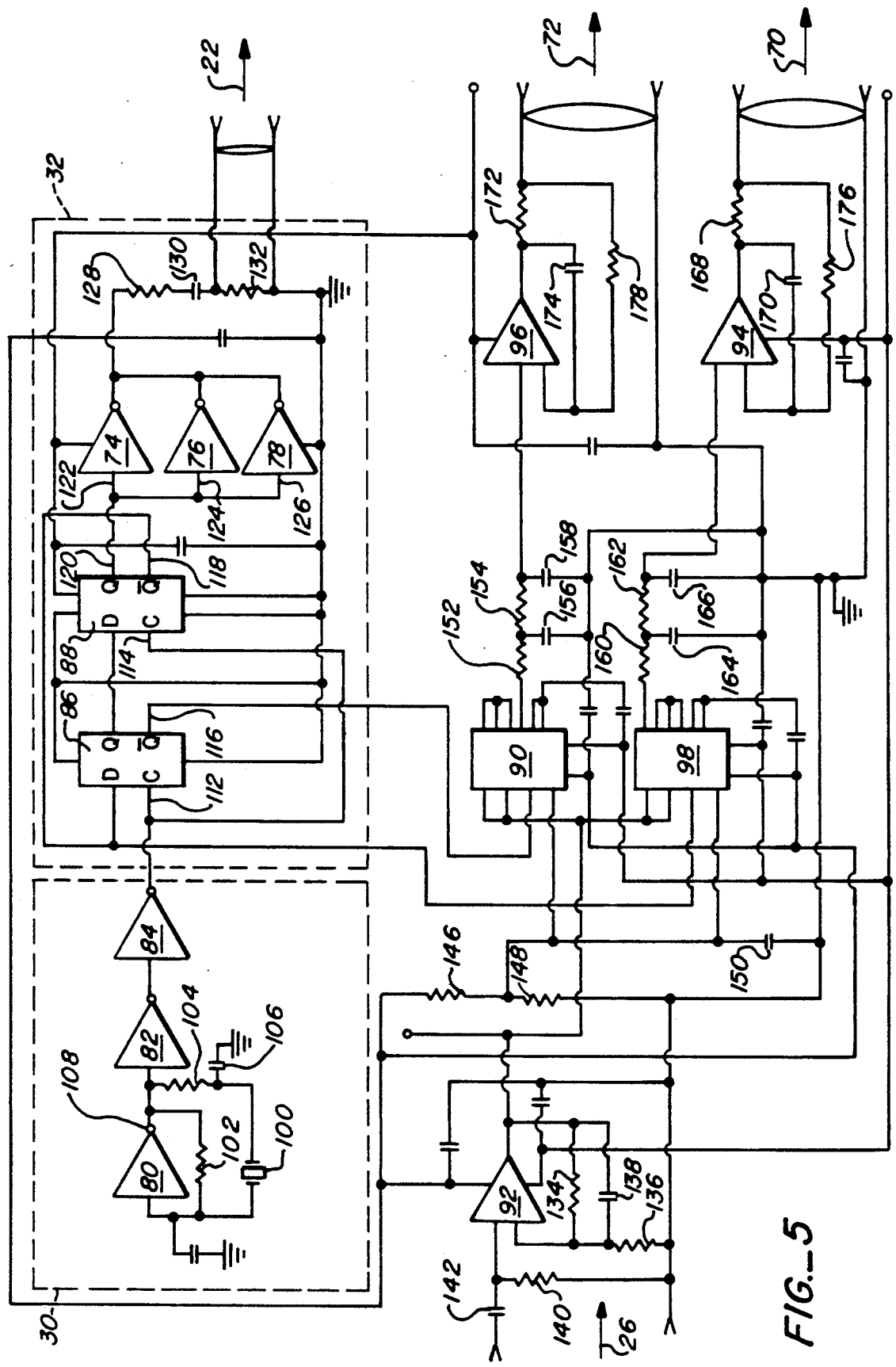
FIG._5

FLAME POSITION ULTRASONIC INTERFEROMETER

This application is a continuation of application Ser. No. 082,780, filed Jul. 27, 1987, now abandoned.

BACKGROUND OF THE INVENTION

1. Field of the Invention

This invention relates to burn front position determination. More particularly, but without limitation thereto, this invention relates to an interferometer for measuring burn front position in a solid propellant by means of sound waves.

2. Description of the Prior Art

Several instruments have been developed for determining burn front position. These operate using electromagnetic radiation, such as the microwave flame front detector.

The present invention functions by utilizing sound waves rather than electromagnetic radiation and there are several advantages to this approach. The present invention, an ultrasonic interferometer, is capable of operating through materials which are opaque to electromagnetic radiation, for example graphite composite materials and steel. Additionally, there is a greater usable depth of penetration and the data generated is easier to analyze. The ultrasonic interferometer operates on a shorter wavelength than microwave flame front detectors currently in use and it requires no adjustments to be made during operation.

SUMMARY OF THE INVENTION

An object of the present invention is to develop a means for measuring the burn front position in a solid rocket propellant.

A further object of the present invention is to develop an interferometer which is operable through a wide range of motor casing materials, such as graphite composites.

These and other objects have been demonstrated by the present invention wherein separate adjacent transmitter and receiver elements are attached to the motor casing whereby the elements form a coupling minimized ultrasonic interferometer system. An ultrasonic beam is transmitted to the motor's interior and the reflected beam from the propellant-gas (burn front) interface is captured by the receiver. The received signal is further processed to determine the distance to the propellant-gas interface. The invention will be described in further detail with reference to the accompanying drawing wherein:

BRIEF DESCRIPTION OF THE DRAWING

FIG. 1 is a schematic representation of the invention;

FIG. 2 is a simplified block diagram of the operation of the ultrasonic interferometer;

FIG. 3 is an illustration representing typical output data obtained from the operation of the ultrasonic interferometer;

FIG. 4 is an illustration representing typical output data, 90 degrees out of phase from the data in FIG. 3 and;

FIG. 5 is a schematic circuit diagram of the invention.

FIG. 6 is a schematic circuit diagram of the power source for the invention.

DESCRIPTION OF THE PREFERRED EMBODIMENT

The ultrasonic interferometer shown in FIG. 1 employs a special dual ultrasonic transducer comprised of a transmitting transducer 10 and a receiving transducer 12 positioned adjacent to each other and affixed to the external surface 14 of the rocket motor. A beam of high frequency sound is coupled into the motor, passing through the motor case 16, the insulator 18 and the propellant 20. The sound beam is transmitted along the path of acoustic signal 22 and is partially reflected by the propellant-gas interface 24, this interface being the location of the burn front. The reflected beam is directed along a path 26 and is received and converted to an electrical signal, the magnitude of which corresponds to that of the reflected signal. This electrical signal is then processed to determine the distance "X" between the rocket motor surface 14 and the propellant-gas interface 24.

Separate transducer elements are used for transmitting the beam and receiving the reflected beam in order to minimize unwanted coupling. This is shown in the block diagram of FIG. 2. The transmitted beam, of a selected frequency traveling along conductor 28, is a 250 kHz sinusoid, for example, generated by oscillator 30. The transmitted beam is then amplified by an amplifier 32 and is applied to the input of transducer 10 that generates acoustic signal 22.

The reflected acoustic signal, traveling along path 26, is also a 250 kHz sinusoid. The reflected acoustic signal is converted to electrical signal by transducer 12 and is then amplified by preamplifier 34 having parallel outputs 36 and 38. Each of the received parallel signals is multiplied by a sample of the transmitted signal. Output signal 36 is applied to the input of multiplier 40 where it is multiplied by a first sample that is connected directly to the output of oscillator 30. Output signal 38 is applied to the input of multiplier 44 where it is multiplied by the output of phase shifter 48 which provides a 90° ($\pi/2$) phase shift of the output from oscillator 30. It should be noted that multipliers 40 and 44 also function as demodulators. The multiplied and demodulated signals from multipliers 40 and 44 then respectively pass through low pass filters 54 and 56 and provide output signals 70 and 72. The transmitted signal $S_o$ along path 22 is given by:

$$S_o = \cos(2\pi f t) \tag{1}$$

where
f = the excitation frequency and
t = time

There are numerous reflections in addition to the desired one which is directed along path 26. For example, transmitted signals (i.e. $S_i$, see equation (3) traveling along path 58 reach the case to insulator interface 60 and are reflected along path 62 to receiving transducer 12. In addition, transmitted signals traveling along path 64 reach the insulator to propellant interface 66 and are reflected along path 68 to receiving transducer 12. There is also coupling through the transducer mounting and shear wave coupling through the case. Very little intermodulation occurs due to the fact that the system is sufficiently linear. Therefore, the signals received at the receiving transducer 12 can be summed by the following equation:

$$S_R = \Sigma S_i \quad (2)$$

where
$S_R$ = the total received signal and
$S_i$ = each individual signal given by:

$$S_i = K_i \cos(2\pi ft + \phi_i) \quad (3)$$

where
$K_i$ = a constant representing the attenuation of the beam that is reflected and
$\phi_i$ = the phase shift.

The phase shift is further defined by the following equation:

$$\phi_i = \frac{(2\pi f)}{v} L + \phi_o \quad (4)$$

where
where v = the velocity of the propagation sound
L = the path length which the sound traverses and
$\phi_o$ = a constant which is the result of time delays in the tranducers and electronics.

Assuming that the demodulation process is linear, then each reflection can be examined separately due to the principle of superposition. The demodulation process used is a good approximation of the Fourier frequency shift function which can be shown to be linear. A first demodulator 40 multiplies the received signal (i.e. $S_i$, see equation (3) by Cos ($2\pi ft$) giving:

$$\cos(2\pi ft)\cdot S_i = K_i \cos(2\pi ft + \phi_i)\cdot \cos(2\pi ft) \quad (5)$$

$$= K_i \cos(\phi_i) + K_i \cos(4\pi ft + \phi_i) \quad (6)$$

The low pass filter 54 will remove the second term, leaving:

$$A_i = K_i \cos(\phi_i) \quad (7)$$

where $A_i$ = the filtered signal of the first multiplier 40. Likewise, a second multiplier 44 multiplies the received signal by Sin ($2\pi ft$) rather than by the Cosine as with multiplier 40 thereby, giving:

$$\sin(2\pi ft)\cdot S_i = K_i \cos(2\pi ft + \phi_i)\cdot \sin(2\pi ft) \quad (8)$$

$$= K_i \sin(\phi_i) - \cos(4\pi ft = \phi_i) \quad (9)$$

The low pass filter 56 removes the second term, leaving:

$$B_i = K_i \sin(\phi_i) \quad (10)$$

where $B_i$ = the filtered signal of the second multiplier 44.

This presumes that the multipliers 40 and 44, and the low pass filters 54 and 56 have well matched gains. The signals at all the $S_i$'s except the desired one are either constant or a weak function of pressure (due to small dimensional changes in the motor). Therefore, their contribution to the output is a small function of pressure (f(P)), plus a constant (C). Invoking superposition and combining equation (4) with (7) and (10) yields:

$$A_i = K\phi \cos\left(\left(\frac{4\pi f}{v}\right)X + \phi_o\right) + f_A(P) + C_A \quad (11)$$

$$B_i = K\phi \sin\left(\left(\frac{4\pi f}{v}\right)K + \phi_o\right) + f_B(P) + C_B \quad (12)$$

where $2X = L \quad (13)$

FIGS. 3 and 4 are plots of typical data from a test firing. FIG. 3 represents the output signal 70 (with carrier removed) from low pass filter 54 and FIG. 4 represents the output signal 72 (with carrier removed) from filter 56, which is 90 degrees out of phase.

The highest significant frequency expected is dependent upon the maximum expected burn rate R, and is given by the following equation:

$$f_{max} = \left(\frac{2f}{v}\right) R \quad (14)$$

$$\text{where } \frac{2f}{v} = \left(\frac{v}{2f}\right)^{-1} = (0.12 \text{ in/cycle})^{-1} \quad (15)$$

For a maximum burn rate of 1 in/sec, the highest significant frequency is 8 Hz. Frequencies higher than 8 Hz represent noise in the data, motor vibrations etc and as such, should be eliminated from consideration.

During the initial portion of the burn, the propellant is thick enough that the sound is dissipated in the propellant and the constant $K_i$ is very small. The output during the initial portion of the burn is just an offset plus a small function of pressure.

As the burn progresses and the $K_i$ value increases, the output becomes an increasing sine wave whose envelope or amplitude is dependent upon Ki. The offset is the same as at the beginning of the firing. Since frequency is the derivative of phase, frequency varies proportionally to the burn rate. Each cycle of the sine wave represents a change in propellant thickness of (v/2f) between cycles. A typical value for v/2f is about 0.1 inch per cycle.

When the burn reaches the insulator 18, the-rate of change in thickness decreases since the insulator rubber burns more slowly than the propellant. If the flame arrives at the insulator at an oblique angle there is little or no reflected signal before the flame arrival. However, at the time of flame arrival there is a large change in at least one of the output channels.

The purpose of having two output signals 70 and 72 is partially for redundancy. However, the second (quadrature) channel or signal 72 contains valuable information since the system is linear in that there are no cross products of the signals from different reflections. Further, the gain of the two channels is well matched and their phase separation is accurate. Because of these characteristics it is possible to extract additional information from the signals. For example, if the various offset terms are subtracted out, the following equations would remain:

$$\frac{A_i - \text{offsets}}{B_i - \text{offsets}} = \tan\left(\left(\frac{4\pi f}{v}\right)X + \phi_o\right) \quad (16)$$

and

-continued $$X = \left(\frac{v}{4\pi f}\right)\left[\text{Tan}^{-1}\left(\frac{A_{i-\text{offsets}}}{B_{i-\text{offsets}}}\right) - \phi_o\right] + n\left(\frac{v}{2f}\right) \quad (17)$$

where n=the number of sine wave cycles which can be determined by counting cycles from the beginning or end of the burn as shown, for example in FIGS. 3 and 4. The K term drops out, providing a better representation of the burn rate. From equation (17) it can be seen that the relative displacement of the burn front can be determined.

Data reduction may serve other purposes. As estimate of K, the magnitude of the reflection, can be obtained by taking the square root of the sum of the squares of the two channels. Assuming the bias has been correctly removed and the gains are well matched, this plot has very little periodic variation. Additionally, this plot contains information about insulator char. The separate channel data may also be normalized by dividing them by the magnitude (K) as calculated above. These plots make changes in the burn rate more obvious because the amplitude information has been removed.

Further, the Fourier transform can be applied to the raw data. This is a complex transform using one channel for the real part and the other channel for the imaginary part. The data must first be divided into segments, the length of which determines frequency resolution. An effect of the Fourier transform is to separate signals that had previously been summed thus separating the signals from the various reflections. Should the resulting transforms be presented in a pseudo three dimensional or waterfall format, the desired signal would be evident. With the magnitude axis representing the size of the reflection, the frequency axis represents velocity.

As has already been noted, this invention is mainly comprised of a transmitter section and a receiver section. The specific components of these sections are illustrated in FIG. 5. In general the transmitter section includes integrated circuits 74, 76, 78, 80, 82, 84, 86 and 88 and the receiver section includes of integrated circuits 90, 92, 94, 96 and 98.

Oscillator 80 provides a 1 megahertz signal, for example, the frequency of which is determined by a quartz crystal resonator 100. Resistor 102 functions to establish the dc bias. The additional phase shift necessary to stabilize the oscillator is provided by a resistor 104 and a capacitor 106. The signal on pin 108 of oscillator 80 is amplified by inverters 82 and 84. The amplified output of the oscillator drives both clock inputs 112 and 114 of flip-flop circuits 86 and 88 respectively. Together circuits 86 and 88 are interconnected to form a divide by four Johnson counter. The outputs on pins 116 and 118 are 250 kilohertz square waves differing in phase by 90 degrees. The function of the counter is twofold: to assure a symmetrical output waveform and to provide quadrature (90 degree phase shift) outputs.

The output on pin 120 of circuit 88, which is the logical compliment of the output on pin 118, drives inverter buffer circuits 74, 76 and 78 respectively. These three CMOS inverter buffers amplify and are added to drive the transmitting transducer to produce an acoustic beam traveling along path 22. The buffers can be connected in parallel since they are well matched as a result of being constructed on the same substrate. Further, the current saturation characteristics of CMOS transistors in the buffers are conducive to parallel connection. Resistor 128 limits output current and aids in matching the cable impedance. Capacitor 130 and resistor 132 remove the dc component of the waveform. Although the output voltage waveform is a square wave, the current in the transmitting transducer is a sinusiod.

The transducers are specifically designed for continuous wave operation. They have a fairly high Q at resonance and their higher order modes are well suppressed. The acoustic wave which is transmitted into the chamber is therefore of substantially sine wave configuration.

The received acoustic signal 26 is amplified by an operational amplifier 92 which is connected as a noninverting amplifier. The gain is set by resistors 134 and 136. Capacitor 138 compensates for stray input capacitance. Resistor 140 sets the input impedance and supplies bias current to the amplifier 92. The electrical signal from transducer 12 is capacitively coupled by capacitor 142 to amplifier 92. The amplified signal from amplifier 92 is connected in parallel to the signal inputs of balanced demodulators 90 and 98 which function as multipliers. The reference inputs of demodulators 90 and 98 are quadrature square waves from pins 116 and 118 of circuits 86 and 88, respectively.

A voltage divider is comprised of resistor 146, resistor 148 and capacitor 150. This divider operates to provide a voltage reference level for demodulators 90 and 98. The output of demodulator 90 is filtered by low pass filters comprising two resistors 152 and 154, and two capacitors, 156 and 158. Likewise, the output of demodulator 98 is filtered by low pass filters comprising two resistors 160 and 162, and two capacitors 164 and 166.

The demodulated signal outputs are driven by a dual operational amplifier 94 and 96, which are respectively connected as two independent voltage followers. The load of amplifier 94 is isolated by resistor 168 and capacitor 170, and that of amplifier 94 by resistor 172 and capacitor 174. Resistors 176 and 178 act to compensate for the voltage developed across resistors 152, 154, 160 and 162 by the input bias currents of amplifiers 94 and 96.

Power is supplied by a dc to dc converter module 180, as is shown in FIG. 6. A diode 182 protects the converter 180 from excessive or reversed input voltage. A resistor 184 references the output common to ground and a capacitor 186 provides a low impedance path for the high frequencies between the output common and ground. The remaining capacitors 188 and 190, act to bypass high frequency currents around the power supplies.

This invention has been discribed in detail with particular reference to certain preferred embodiments thereof, but it will be understood that variations and modifications can be effected within the spirit and scope of the invention.

What is claimed is:

1. A method for measuring the burn front position located at the solid-gas interface of a rocket motor having an external surface, comprising the steps of:
    (a) placing a transmitting transducer on said rocket motor external surface;
    (b) placing a receiving transducer on said rocket motor external surface;
    (c) generating a first electrical signal of a selected frequency;
    (d) generating a first acoustic signal in said transmitting transducer from said first electrical signal;
    (e) transmitting said first acoustic signal into said rocket motor from said transmitting transducer to reflect off said solid-gas interface as a reflected acoustic signal;

(f) receiving said reflected acoustic signal at said receiving transducer and converting said reflected acoustic signal into a second electrical signal;

(g) generating a third electrical signal by multiplying said second electrical signal with said first electrical signal and (h) calculating the distance between said rocket motor surface and said solid-gas interface from said third electrical signal.

2. The method of claim 1 wherein:
said solid-gas interface is a propellant-gas interface.

3. The method of claim 1 wherein:
said solid-gas interface is an insulator-gas interface.

4. The method of claim 1 wherein said step (g) includes generating a fourth electrical signal by passing said first signal through a ninety degree phase shifting means, and then generating a fifth electrical signal by multiplying said second electrical signal with said fourth electrical signal, and step (h) includes calculating the distance between said rocket motor surface and said solid-gas interface from said third and fifth electrical signals.

5. The method of claim 4 wherein said step (h) includes the sub-step of first passing said third and fifth electrical signals through first and second low pass filters, respectively, before calculating the distance between said rocket motor surface and said solid gas interface from said third and fifth electrical signals.

6. The method of claim 5 wherein said step (h) of calculating the distance between said rocket motor surface and said solid-gas interface from said third and fifth electrical signals and which includes the sub-step of passing said third and fifth electrical signals through first and second low pass filters, respectively, includes the sub-step removing constant bias signals from said third and fifth electrical signals to produce sixth and seventh electrical signals.

7. A flame position sensor for measuring the burn front position located at the solid-gas interface of a rocket motor having an external surface, comprising:
an oscillator means for generating a first electrical signal of a selected frequency;
a transmitting transducer for converting said first electrical signal into an acoustic signal of the same frequency, said transmitting transducer being mounted on said rocket motor external surface;
a receiving transducer for converting an acoustic signal reflected off said solid gas interface into a second electrical signal, said receiving transducer being mounted on said rocket motor external surface;
signal processing means for computing a new electrical signal from input signals, said signal processing means including
a first signal multiplier, the output of said oscillator means being applied to an input of said first signal multiplier, an input of said first multiplier, said second electrical signal output of said receiving transducer being applied to an input of said first signal multiplier, said new electrical signal which is an output of said first multiplier being made available to facilitate computation of the distance between said rocket motor surface and said solid-gas interface.

8. The apparatus of claim 7 including second signal processing means for computing a second new electrical signal from said first and second electrical signals, said second signal processing means including
a second multiplier and a ninety degree phase shifting means, said first electrical signal being applied to an input of said ninety degree phase shifting means, an output of said ninety degree phase shifting means being applied to an input of said second multiplier, said second electrical signal being applied to an input of said second multiplier, said first and second new electrical signals being made available to facilitate computation of the distance between said rocket motor surface and said solid-gas interface.

9. The apparatus of claim 8 including means for computing a third new electrical signal from input signals includes first and second low pass filters receiving said first and second new electrical signals.

10. The apparatus of claim 9 including means for computing a fourth new electrical signal which includes first and second means for removing constant biases used in combination with said first and second low pass filter means, respectively.

11. The apparatus of claim 10 including means for computing arctangents of ratios of signals.

12. A flame position sensor for measuring the burn front position located at the solid-gas interface of a rocket motor having an external surface, comprising:
an oscillator means for generating a first electric signal of a selected frequency;
an amplifier, an output of said oscillator being connected to an input of said amplifier;
a transmitting transducer for converting an electrical signal output from said first amplifier into an acoustic signal of the same frequency, said
transmitting transducer being mounted on said rocket motor external surface for transmitting the acoustic signal into the rocket motor to reflect off said solid-gas interface;
a receiving transducer for converting an acoustic signal reflected off said solid-gas interface into a second electrical signal, said receiving transducer being mounted on said rocket motor external surface;
signal processing means for computing from said first and second electrical signals as input signals, said signal processing means including
a ninety degree phase shift device,
a second amplifier,
a first signal multiplier,
a second signal multiplier,
a first low pass filter means,
a second low pass filter means,
a first bias removal means,
a second bias removal means, and
arctangent computation means for computing the arctangent of a signal, said first electrical signal being applied to an input of said first multiplier and through said ninety degree phase shift device to an input of said second multiplier, said second electrical signal being applied through said second amplifier to inputs of said first and second multipliers, outputs of said first and second multipliers being applied to said first and second low pass filter and first and second bias removal means, outputs of said bias removal means being applied to said arctangent computation means to facilitate computation of the distance between said rocket motor surface and said solid-gas interface.

* * * * *